United States Patent [19]

Switzgable

[11] 4,090,940
[45] May 23, 1978

[54] APPARATUS FOR PRODUCING METHANE GAS BY PROCESSING WASTE MATERIALS

[75] Inventor: Harold Switzgable, Monmouth Junction, N.J.

[73] Assignee: Alpha Systems Corporation, Monmouth Junction, N.J.

[21] Appl. No.: 651,982

[22] Filed: Jan. 23, 1976

Related U.S. Application Data

[62] Division of Ser. No. 499,751, Aug. 22, 1974, abandoned.

[51] Int. Cl.² .................... C02B 5/12; C25B 3/02; C25B 9/00
[52] U.S. Cl. .................... 204/278; 204/149; 204/157.15; 204/270; 204/273; 204/274; 204/275; 210/12
[58] Field of Search .............. 204/149, 52, 72, 157.15, 204/158 R, 162 R, 278, 270, 273, 274, 275, 279; 210/12, 16, 44, 403, 525, 195

[56] References Cited

U.S. PATENT DOCUMENTS

| 2,813,074 | 11/1957 | Banks | 210/525 |
|---|---|---|---|
| 3,336,220 | 8/1967 | Neidl | 204/149 |
| 3,616,436 | 10/1971 | Haas | 204/278 X |
| 3,642,605 | 2/1972 | Chenel et al. | 204/300 |
| 3,664,940 | 5/1972 | Greyson et al. | 204/300 X |
| 3,761,221 | 9/1973 | Stillions | 204/278 X |
| 3,846,300 | 11/1974 | Inoue | 204/149 X |

*Primary Examiner*—Arthur C. Prescott
*Attorney, Agent, or Firm*—Albert Sperry; Frederick A. Zoda; John J. Kane

[57] ABSTRACT

Apparatus for producing methane and other products by processing a slurry of biodegradable waste materials including two tanks containing waste material which are connected to allow fluid flow communication between slurry in each tank, each tank being airtight with respect to the ambient, one of said tanks containing a cathode and the other tank containing an anode to aid in the growth of methane producing bacteria, the tanks provided with movable hoods for collecting gas.

30 Claims, 2 Drawing Figures

APPARATUS FOR PRODUCING METHANE GAS BY PROCESSING WASTE MATERIALS

The present application is a division of U.S. Ser. No. 499,751, filed Aug. 22, 1974 now abandoned.

BACKGROUND OF THE INVENTION

1. Field of Invention

This invention applies generally to the field of recycling waste material to produce easily harnessed energy sources. The current energy shortage has magnified this need for alternative energy sources. This invention provides a method and apparatus whereby all the waste material from a particular area except metals and certain plastics can be recycled to produce methane gas and other by-products.

The present invention has applications in both commercial and household systems. If a large source of waste material is available such as a garbage dump or a farm, it will be possible with this invention to commercially produce great volumes of methane gas without the addition of any significant amount of energy. In individual household applications this invention can be utilized to process the waste materials from almost all the domestic sources such as human wastes, pet wastes, grass and shrubbery cuttings, discarded food, residue from garbage disposals, and dry paper product trash excluding metals and some plastics. In this manner the particular household could have a source of energy for powering air-conditioning units, heating units, hot water heaters, household electrical appliances, lawn mowers, household automobiles, and other sundry household items. This system would be especially desirable due to the rapidly increasing cost of electricity.

2. Description of the Prior Art

Systems for decomposing waste material utilizing anaerobic and aerobic bacteria are old in the art. Over the years these systems have not been subject to refinements and improvements due to the seemingly unlimited sources of energy such as electricity and fossil fuels. Most prior systems have been backyard systems with relatively little sophistication. However, this invention applies some new principles to the prior systems.

The prior art does disclose the use of electrolysis through the slurry solution to increase the bacterial decomposition of the waste material. An example of such a system is U.S. Pat. No. 3,336,220 issued to G. Neidl on Aug. 15, 1967.

Other examples of the prior art which deals with methane gas production are exemplified in the following U.S. Patents:

1,880,772; Buswell
2,262,576; Durdin
3,640,846; Johnson

One problem associated with the prior art was that the oxygen produced by the electrolysis reaction tended to inhibit the growth of the anaerobic bacteria. The present invention overcomes this problem and yet still allows for the use of electrolysis to increase the bacterial growth. Another problem associated with the prior art was the accumulation of unprocessible or processed floating waste materials suspended at the surface of the slurry solution. These relatively inert substances inhibited the production of methane by essentially insulating the slurry solution from the gaseous section of the airtight tank. Accordingly, this invention claims several embodiments for facilitating the removal of these floating waste materials which thereby increases the interface area between the gaseous and liquid materials in each tank.

The prior art utilized various methods of collecting gas and of controlling the level of the slurry in the tanks which were inefficient and cumbersome. This invention encompasses methods and apparatus which increase the efficiency and effectiveness of the gas collecting process.

SUMMARY OF THE INVENTION

This invention utilizes a plurality of tanks. Each of the tanks is covered with a floating hood which seals the contents of the tanks with respect to the ambient. Inside each tank is a slurry solution which consists essentially of a composite of waste materials being partly solid and partly liquid. The volume of slurry in each tank is controlled such that a region exists under the hood for collecting gaseous materials.

One of the tanks is provided with a cathode which is mounted inside the tank such that it protrudes into the slurry solution. Another tank is provided with an anode which also extends into the slurry solution in that tank. The anode tank and the cathode tank are joined by a conduit which connects the tanks at a point in the tank wall below the level of the slurry in each tank such that although the slurry solution in the two tanks is interconnected the gaseous portion of each tank is sealed with respect to each other and with respect to the ambient.

The floating hood of each tank is provided with a means for withdrawing the gas collected therein whenever the hood is vertically moved to a predetermined position. Preferably, at this predetermined height a compressor will be activated which will pump the collected methane or other gas out of the hood and the compressor will cease operation when the hood returns below a predetermined level. This compressor system can be utilized in each tank.

Each tank is provided with an auxilliary inlet and an auxilliary outlet for the introduction of additional new waste material and for the elimination of unprocessible and processed waste material.

The advantage of the apparatus of this invention is that the cathode tank will be sealed with respect to the ambient and with respect to the anode and thereby prevent any oxygen from entering this tank and inhibiting the growth of the anaerobic bacteria. Therefore, the anaerobic bacteria will be able to grow at will and increase the rate of production of methane. Also, in the cathode tank in accordance with standard electrolysis reation, hydrogen gas will be produced. This hydrogen gas will aid in the operation of this tank in two ways. Firstly, any free carbon in the cathode tank will tend to associate with the hydrogen thereby producing additional methane. Secondly, the hydrogen produced in the cathode tank has been shown to be an effective element to aid in the growth and reproduction of certain anaerobic bacteria.

In the anode tank in accordance with the electrolysis reaction oxygen will be produced. This oxygen introduced into the gaseous volume of the second tank is useful in aiding in the growth of aerobic bacteria. It is also desirable that this oxygen is separated from the cathode tank since it would inherently inhibit the growth of anaerobic bacteria therein. Alternatively, in the anode tank the oxygen could be continually pumped off and thereby allow for the growth of anaerobic bacteria in the anode tank, or, of course, the oxygen could be contained therein to aid in the growth of aerobic bacteria.

The two tanks are interconnected below the slurry level by a conduit which allows the free flow of ions due to the electrolysis reaction. The location of this conduit, however, eliminates any possibility of fluid flow communication between the gaseous sections of the cathode tank and the anode tank which would obviously inhibit the bacterial action in each tank.

In addition a method of removing the unprocessible floating slurry from the tanks is shown in this invention. A skimming system can be utilized to eliminate the floating sludge and thereby facilitate contact between the tank atmosphere and the tank slurry. Also, the floating sludge material can be more evenly distributed throughout the slurry solution by the use of agitation and then strained and expelled from the tank.

Each tank can be provided with resistance heater elements to increase the temperature above room temperature to facilitate bacterial growth.

It is an object of this invention to provide a conveniently easily tapped source of recycleable energy.

It is an object of this invention to provide a method for processing waste materials to provide a source of energy and thereby reduce the waste materials into an effective fertilizer solution.

It is an object of this invention to provide a waste recycling process which produces methane gas and other products.

It is an object of this invention to provide a method for producing methane gas that can be utilized by average family household as an energy source.

It is an object of this invention to provide an apparatus for efficiently facilitating the growth of anaerobic and aerobic bacteria within waste material solutions such that methane gas is produced.

It is an object of this invention to provide an economical source of energy which can be utilized on a commercial or on an individual basis.

It is an object of this invention to process biodegradable wastes without the pollution of the natural environment.

It is an object of this invention to provide a method and apparatus for processing waste materials which includes the by-product of hydrogen and/or oxygen gas.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

DETAILED DESCRIPTION OF THE PREFERRED EMBODIMENT

Figure 1:
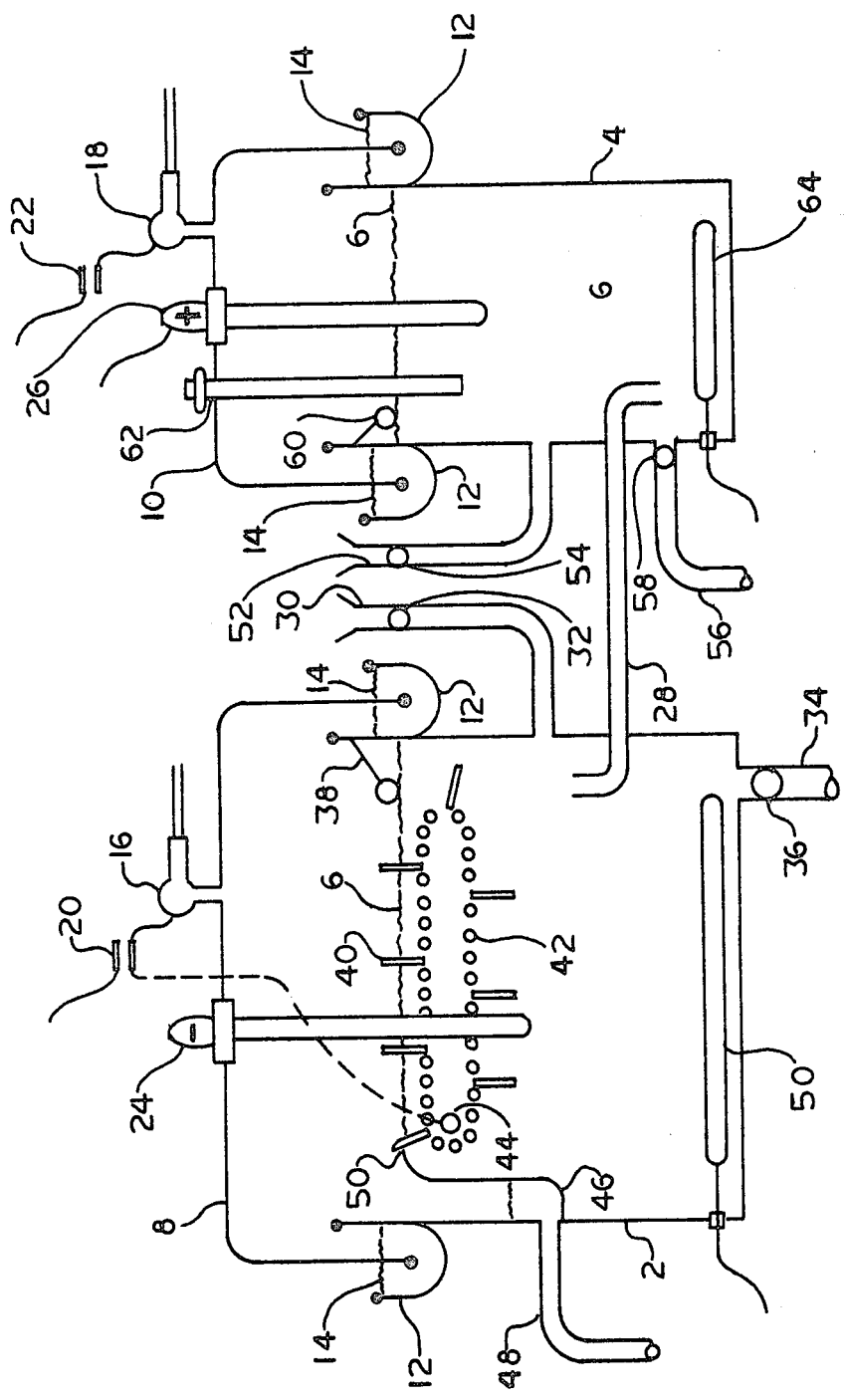
FIG. 1 is a schematic representation of an embodiment of the present invention.

In the embodiment illustrated in FIG. 1 a two tank system is employed, referenced generally as tank 2 and tank 4. Both tanks are shown containing the normal amount of slurry 6 contained therein. The slurry consists of a large variety of waste materials, the exact composition of which is determined by the particular commercial or household application involved.

Tanks 2 and 4 are provided with the vertically movable hoods 8 and 10, respectively. These hoods are shown suspended in channels 12 which contain therein an oil solution 14. The channel 12 extends around the entire periphery of the tank so that by utilizing the sealing properties of the oil channel the internal environment of the tanks will be hermetically sealed with respect to the ambient. In this manner elements can be excluded from the tank environment which may be detrimental to the growth of the particular bacteria being cultivated therein.

Tank 2 is provided with a compressor 16 for removing gas accumulated within hood 8 of tank 2. Similarly hood 10 is equipped with compressor 18 for withdrawing gas accumulated under hood 10. Associated with compressors 16 and 18 are switches 20 and 22, respectively, which serve to activate the compressors whenever the hoods 8 and 10 move vertically in response to an accumulation of gases lighter than air therein to a predetermined vertical position such that a switch is closed. Upon closing of either of these switches the associated compressor is activated to withdraw the gas accumulated within the particular hood and thereby allow the associated hood to again move downward. The moving downward thereby releases the switch and thereby ceases the operation of the associated compressor. Tank 2 is provided with a cathode element 24 which is mounted such that it protrudes into the slurry solution when filled at the normal level. Similarly tank 4 is provided with an anode 26 which is mounted such that it protrudes into the slurry solution located in tank 4. Tanks 2 and 4 are interconnected by conduit 28. This conduit provides fluid flow communication between the slurry located in each tank. The conduit 28 is positioned in the walls of tanks 2 and 4 such that it is completely below the normal level of the slurry to prevent any flow communication of the gases located in the upper portions of tanks 2 and 4. The conduit 28 is of sufficient size to permit the flow of ions between cathode 24 and anode 26, which allows the electrolysis action to take place whenever direct current or alternating current is applied to electrodes 24 and 26.

Tank 2 is provided with an inlet 30 and an inlet valve 32 to allow and control and input of additional waste material into the slurry solution located within tank 2. Additionally, tank 2 is provided with an outlet 34 and outlet valve 36 for the exhaust of processed and unprocessible slurry matter. Valves 32 and 36 can be associated with sensing element 38. Sensing element 38 is responsive to the level of the slurry solution located in tank 2 such that when the level of the solution becomes sufficiently low valve 32 admits additional fresh slurry. Sensing element 38 is also provided such that if the level of slurry solution in tank 2 becomes sufficiently high valve 36 will open and thereby exhaust part of the slurry solution.

Figure 2:
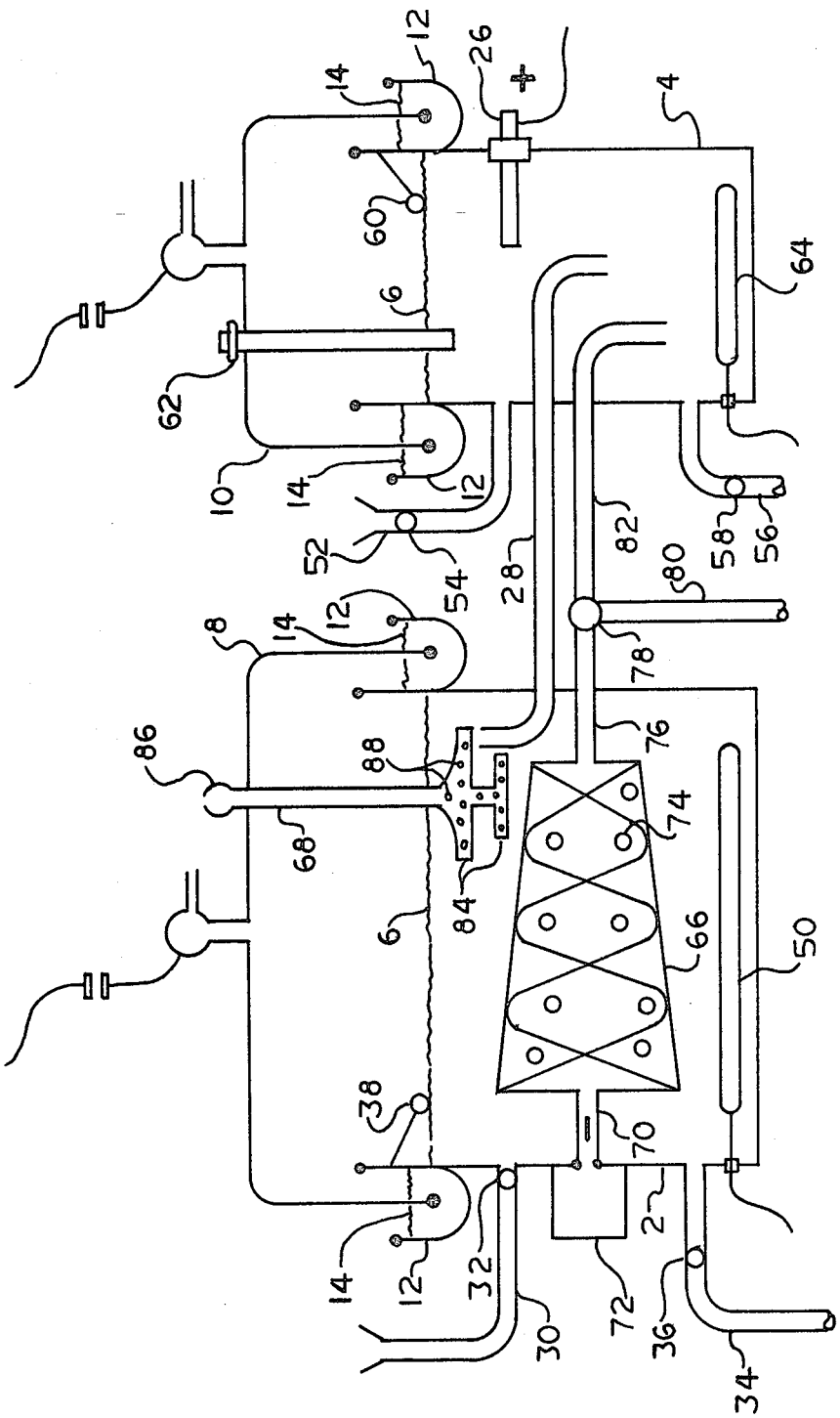
FIG. 2 is a schematic diagram of another embodiment of the present invention.

The maintenance of a constant level of slurry solution is important due to the action of wiper elements 40. Wiper elements 40 are mounted on chain drive element 42. Chain drive element 42 is driven by motor 44. Whenever motor 44 is actuated chain drive element 42 operates in a counterclockwise manner such that wiper elements 40 skim along the surface of the slurry solution of tank 2. Part of the cross-section of wiper element 40 is above the top surface of the liquid slurry solution and part of the wiper element moves along below the level of the liquid slurry solution when moving toward trough 46. In this manner wiper element 40 picks up all the processed and unprocessible floating sludge on the surface of the slurry solution. The wipers which are partly located above the surface as they move to the left as shown in FIG. 2 push this floating sludge into trough 46 and it is thereby exhausted through drain 48. As the wipers each contact trough 46 at protruding edge 50 they wipe the floating surface sludge into the trough by being urged against the leading edge 50. After an individual wiper passes the leading edge 50 it is then returned back to the right edge of the tank along a a path slightly submerged from the surface as shown in FIG. 1. These wipers 40 are preferably made with disposable rubber sections which form the contact with leading edge 50 of trough 56 during each revolution of the chain 42.

The formation of sludge is usually in direct proportion to the amount of methane gas given off from the slurry solution. To prevent the consumption of excess energy by motor 44 it is connected to its power source through switch 20. Therefore, the motor 44 rotates chain 42 in a counterclockwise direction only during the intermittent periods when compressor 16 is also activated. As discussed before this occurs whenever the hood 8 moves to a predetermined vertical height. In addition whenever the switch 20 is opened and compressor 16 thereby ceases action motor 44 will also cease rotating chain 42.

Tank 2 can be equipped with an auxiliary unit 50 therein such as a heater element which is used to elevate the temperature of slurry solution 6 above the normal ambient temperature. It has been found that to promote the production of methane that temperatures in the range of 90° F to 100° F have been most effective.

Tank 4 is similar to the configuration of tank 2 in that inlet 52 has a valve 54 which is used for the introduction of additional fresh slurry solution. Also, outlet 56 has an outlet valve 58 which is used for expelling processed and unprocessible slurry materials. A sensing device 60 is used to sense the level of the slurry solution and, as in tank 2 maintains the proper level by the control of valves 54 and 58.

Tank 4 is equipped with bubbling element 62 which can be used to introduce gas, such as air to oxygen into the slurry solution in tank 4 to increase the oxygen content thereof. In this manner element 62 can increase the growth of any aerobic bacteria located in tank 4. Tank 4 is equipped with an auxilliary unit 64 such as a heating element which can be used to control the temperature of slurry solution 6 located in tank 4.

Auxilliary units 50 and 64 could be a light-emitting element which when actuated introduces energy into the tanks 2 and 4 in the form of photon energy. Since the introduction of electrical lines to units 50 and 64 might become shorted in time by the breakdown of the electrical insulation and the like it might prove advantageous to use "light tubes" or "fiberoptics" (not shown) to convey the light from an external source to the interior of tanks 2 and 4. Also additional energy could be introduced into the waste material located in tanks 2 and 4 by closing units 50 and 64 to be ultrasonic tranducers to emit ultrasonic waves into the waste solution and thereby increase the temperature thereof.

At this point it should be noted that a power source will be required for various elements in this system such as units 50 and 64, the electricity source for cathode 24 and anode 26, power sources for compressors 16 and 18, and other various drives necessary for this system. Preferably these power sources will utilize methane as a fuel or in the alternative will utilize a free energy source such as wind by using a windmill. Also the oxygen produced in tank 2 by cathode 26 when drawn off by compressor 18, can be used to power an oxygen consuming fuel cell or other similar device which converts the oxygen into electrical energy to effect the electrolysis reaction.

FIG. 2 illustrates another embodiment of the present invention using certain alternative configurations. The primary difference between these embodiments is the differing apparatus for removing the processed and unprocessible floating and non-floating sludge materials from tank 2.

Generally, in FIG. 2 the barrel 66 collects and expels the undesirable sludge material. In addition, barrel 66 functions as the cathode suspended in the slurry 6. For this use the barrel will most likely be formed of a metal material.

Since much of the exhausted slurry material will float on the surface it is necessary to agitate the solution. This agitation is accomplished through the rotation of barrel 66 and by the vertical movement of tree 68. Barrel 66 is connected by drive shaft 70 to motor 72. Motor 72 is reversible such that barrel 66 can be rotated in a first direction and in a second direction. Barrel 66 is tapered with internal fins (not shown) and perforations 74 such that when the barrel 66 is rotated in a first direction, any solid sludge materials located therein will be contained within barrel 66 while it is rotated and any liquid fresh slurry will be expelled through holes 74. This straining operation will keep solidified unprocessible and processed waste materials within barrel 66 during rotation in the first direction. If motor 72 is reversed such that barrel 66 rotates in a second direction the internal fins will urge all material located therein through outlet channel 76 to valve 78. The operation of barrel 66 is similar to that of a common cement truck tank. Once the material being exhausted by barrel 66 has reached valve 78 it can selectively be channeled into exhaust channel 80 for disposal or into channel 82 which will discharge this material into tank 4 for further processing.

The rotation of barrel 66 will also serve to agitate the slurry solution located in tank 2 such that the waste materials which the operator is desirous of expelling will be more equally distributed throughout the slurry solution rather than floating on the surface. In addition, tree 68 is used to agitate the surface of the slurry solution. Tree 68 is connected to cover 8 in FIG. 2 such that whenever the cover moves up or down in relation to the tank body the tree will break the surface of the slurry solution and thereby agitate it. The tree 68 is provided with flanged portions 84 which aid in this agitation. Alternatively, fresh slurry will be expelled through holes 74. This straining operation will keep solidified unprocessible and processed waste materials within barrel 66 during rotation in the first direction. If motor 72 is reversed such that barrel 66 rotates in a second direction the internal fins will urge all material located therein through outlet channel 76 to valve 78. The operation of barrel 66 is similar to that of a common cement truck tank. Once the material being exhausted by barrel 66 has reached valve 78 it can selectively be channeled into exhaust channel 80 for disposal or into channel 82 which will discharge this material into tank 4 for further processing.

On the operation of this ysstem it is necessary to first form a slurry of the acceptable waste materials. In a household application such materials would include kitchen sink disposal remains, toilet wastes (excess water removed), paper refuse, and all other biodegradable household wastes. With some products containing an abnormally large amount of dissolved or captured oxygen it will be necessary to soak the waste materials prior to introduction into the tanks. This excess oxygen should be eliminated due to its obvious effect on any anaerobic bacteria. This properly soaked solution can then be stored until required by the system.

Initially both tanks are filled to the desired level with the proper amount of slurry waste material. Then each tank receives a charge of bacterial inoculate. This inoculate will vary in relation to the type of waste material most probably expected to be inserted into this system. Usually the inoculate inserted into tank 2 will contain primarily anaerobic bacteria whereas the inoculate applied to tank 4 will contain primarily aerobic bacteria.

The bacterial culture introduced by the inoculate in tank 2 will feed upon the waste material and grow sufficiently such that it will produce a substantial amount of methane gas thereby actuating the system of vertical movement of cover 8. This methane gas will then be collected as described above by compressor 16. In tank 4 the aerobic bacteria will further attack and feed on the solution in the tank and thereby increase the value of the slurry in tank 6 for fertilizer purposes.

The nature of the electrolysis reaction will be such that in the area of the cathode 24 hydrogen gas will be created. This hydrogen gas is beneficial for several reasons. Firstly, any free carbon atoms in tank 2 will readily associate with the hydrogen atoms to thereby create methane.

Secondly, the growth of the anaerobic bacteria in tank 2 will be facilitated since many of these bacteria tend to consume hydrogen in their creation of methane. In tank 4 the gas associated with the electrolysis reaction created at anode 26 will be oxygen. This oxygen can be directly a source of energy if the system is operated such that compressor 18 draws this oxygen off and compresses it. The oxygen produced at anode 26 could be kept in tank 4 such that the growth of the aerobic bacteria in tank 4 would be increased. The growth of the aerobic bacteria would be further increased by the introduction of additional oxygen into solution 6 in tank 4 by the bubbling of oxygen or air through air bubbler 62. As stated previously the benefit of the aerobic bacterial action in tank 4 would be to reduce the slurry to a liquid usable as fertilizer. Similarly the processed and unprocessible waste material from tank 2 could also be used as fertilizer. FIG. 2 illustrates a means whereby the slurry is introduced into tank 2 and it is processed by anaerobic bacteria at which point it is expelled by valve 66 through valve 78 and channel 82 into tank 4. This same slurry solution is now subjected to the action of aerobic bacteria and is reduced to elemental fertilizer.

Tank 4 could be used for the production of anaerobic bacteria. For this purpose compressor 18 would be used to withdraw all oxygen created at anode 26 and bubbler 62 would be omitted In this fashion the tank 4 could be inoculated with an anaerobic bacteria culture thereby facilitating the breakdown of slurry 6 in tank 4 and in addition promoting the creation of methane in tank 4 as well. This methane could be collected by compressor 18.

The raising and lowering of hoods 8 and 10 is possible when methane gas is produced since the specific gravity of methane is approximately one half that of the surrounding air.

At this point it should be noted that the size of conduit 28 is variable. There is a minimum size which this connection must be in order to allow free passage of ions between the anode 26 and cathode 24. If tank 4 is being used to generate aerobic bacteria then conduit 28 should be small enough to prevent any substantial flow of slurry between tanks 2 and 4. If tank 4 is being utilized to generate anaerobic bacteria then conduit 28 can be somewhat larger since the mixing of the slurry from tank 2 and tank 4 would be of no detrimental effect. Essentially the primary importance of conduit 28 is to provide a path for ions between cathode 24 and anode 26 and yet to prevent the introduction of any oxygen into tank 2. Therefore it should be appreciated that tank 4 could be made extemely small in relation to tank 2. In this fashion tank 4 will be serving as merely an anode source. This type of system would be most applicable to commercial situations where large quantities of methane gas are desired.

While two particular embodiments of this invention have been shown in the drawings and described above, it will be apparent, that many changes may be made in the form, arrangement and positioning of various elements of the combination. In consideration thereof it should be understood that preferred embodiments of this invention disclosed herein are intended to be illustrative only and not intended to limit the scope of the invention.

I claim:

1. Apparatus for producing methane gas by processing waste materials comprising:
    a. at least one airtight primary tank containing partially liquid and partially solid waste material inoculated with anaerobic bacteria;
    b. a primary outlet for expelling waste material from said primary tank;
    c. a primary inlet for introducing additional waste material into said primary tank;
    d. a cathode located in said primary tank;
    e. means for withdrawing gas created within said primary tank;
    f. at least one airtight secondary tank containing partially liquid and partially solid waste material inoculated with anaerobic bacteria;
    g. a secondary outlet for expelling waste material from said secondary tank;
    h. a secondary inlet for introducing additional waste material;
    i. an anode located in said secondary tank;
    j. means for withdrawing gas created within said secondary tank;
    k. a conduit providing fluid flow communication between waste material in said primary tank and waste material in said secondary tank; and
    l. means for removing non-processible and processed waste material from said primary tank.

2. The apparatus as defined in Claim 1 wherein said removing means further comprises:
    a. a movable conveyor chain located near the surface of the waste material;
    b. at least one wiper fixedly attached to said chain such that when said chain is moved, said wiper moves along the surface of the waste material skimming away non-processible and processed floating waste material; and c. a trough located adjacent one end of said chain such that non-processible and processed floating waste material is urged into said trough.

3. The apparatus as defined in Claim 1 wherein said removing means comprises:
   a. a barrel assembly which when rotated in a first direction agitates and strains the waste material located therein and when rotated in a second direction expels the processed and non-processible waste material through said primary outlet valve.

4. The apparatus as defined in claim 3 wherein said barrel is said cathode.

5. The apparatus as defined in claim 1 wherein said primary tank includes:
   a. a primary cover, movable vertically in proportion to the amount of gas accumulated therein; and
   b. a primary switch, responsive to a predetermined vertical height of said primary cover to actuate said primary withdrawing means.

6. The apparatus as defined in claim 5 further comprising a primary agitation means activated by the vertical movement of said primary cover.

7. The apparatus as defined in claim 5 wherein said primary removing means is responsive to be actuated by a vertical movement of said primary hood.

8. The apparatus as defined in claim 1 wherein said secondary tank includes:
   a. a secondary cover, movable vertically in proportion to the amount of gas accumulated therein; and
   b. a secondary switch, responsive to a predetermined vertical movement of said secondary cover to actuate said secondary withdrawing means.

9. The apparatus as defined in claim 8 further comprising a secondary agitation means activated by the vertical movement of said secondary cover.

10. The apparatus as defined in claim 1 including a means for introducing oxygen into the waste material located in said secondary tank.

11. The apparatus as defined in claim 1 including means for bubbling the hydrogen produced at said cathode into the slurry in said primary tank.

12. The apparatus as defined in claim 1 including a primary heater element located in said primary tank.

13. The apparatus as defined in claim 1 including a secondary heater element located in said secondary tank.

14. The apparatus as defined in claim 1 wherein said primary withdrawing means and said secondary withdrawing means each include a compressor.

15. The apparatus as defined in claim 1 further comprising ultrasonic tranducers positioned within said primary and secondary tanks to selectively be actuated to stimulate activity of bacteria located therein by the addition of energy.

16. The apparatus as defined in claim 1 further comprising light emitting elements positioned within said primary and secondary tanks to selectively be actuated to stimulate the activity of bacteria located therein by the introduction of energy.

17. The apparatus as defined in claim 16 wherein said removing means further comprises:
   a. a movable conveyor chain located near the surface of the waste material;
   b. at least one wiper fixedly attached to said chain such that when said chain is moved, said wiper moves along the surface of the waste material skimming away non-processible and processed floating waste material; and
   c. a trough located adjacent one end of said chain such that non-processible and processed floating waste material is urged into said trough.

18. The apparatus as defined in claim 16 wherein said removing means comprises:
   a. a barrel assembly which when rotated in a first direction agitates and strains the waste material located therein and when rotated in a second direction expels the proceseed and non-processible waste material through said primary outlet valve.

19. The apparatus as defined in claim 18 wherein said barrel is said cathode.

20. The apparatus as defined in claim 16 wherein said primary tank includes:
   a. a primary cover, movable vertically in proportion to the amount of gas accumulated therein; and
   b. a primary switch, responsive to a predetermined vertical height of said primary cover to actuate said primary withdrawing means.

21. The apparatus as defined in claim 20 further comprising a primary agitation means activated by the vertical movement of said primary cover.

22. The apparatus as defined in claim 20 wherein said primary removing means is responsive to be actuated by a vertical movement of said primary hood.

23. The apparatus as defined in claim 16 wherein said secondary tank includes:
   a. a secondary cover, movable vertically in proportion to the amount of gas accumulated therein; and
   b. a secondary switch, responsive to a predetermined vertical movement of said secondary cover to actuate said secondary withdrawing means.

24. The apparatus as defined in claim 23 further comprising a secondary agitation means activated by the vertical movement of said secondary cover.

25. The apparatus as defined in claim 16 including a means for introducing oxygen into the waste material located in said secondary tank.

26. The apparatus as defined in claim 16 including means for bubbling the hydrogen produced at said cathode into the slurry in said primary tank.

27. The apparatus as defined in claim 16 including a primary heater element located in said primary tank.

28. The apparatus as defined in claim 16 including a secondary heater element located in said secondary tank.

29. The apparatus as defined in claim 16 wherein said primary withdrawing means and said secondary withdrawing means each include a compressor.

30. The apparatus as defined in claim 16 further comprising ultrasonic tranducers positioned within said primary and secondary tanks to selectively be actuated to stimulate activity of bacteria located therein by the addition of energy.

* * * * *